United States Patent [19]

Marazza et al.

[11] Patent Number: 5,382,581
[45] Date of Patent: Jan. 17, 1995

[54] (6R)- AND (6S)-DIASTEREOISOMERS OF AN AMMONIUM SALTS OF $N^5$-METHYL-5,6,7,8-TETRAHYDROFOLIC ACID

[75] Inventors: Fabrizio Marazza, Vico Morcote, Switzerland; Jean Jacques, Paris, France

[73] Assignee: Sapec S.A. fine chemicals, Lugano, Switzerland

[21] Appl. No.: 974,565

[22] Filed: Nov. 13, 1992

Related U.S. Application Data

[62] Division of Ser. No. 683,772, Apr. 11, 1991, Pat. No. 5,194,611.

[30] Foreign Application Priority Data

Apr. 12, 1990 [CH] Switzerland ............... 01255/90-1

[51] Int. Cl.$^6$ ........................................ C07D 475/04
[52] U.S. Cl. ...................................... 514/249; 544/258
[58] Field of Search ........................ 544/258; 514/249

[56] References Cited

U.S. PATENT DOCUMENTS

| | | | |
|---|---|---|---|
| 5,124,452 | 6/1992 | Gennari | 544/258 |
| 5,173,488 | 12/1992 | Haeger | 544/258 |
| 5,223,500 | 6/1993 | Gennari | 514/249 |

FOREIGN PATENT DOCUMENTS

| | | | |
|---|---|---|---|
| 455013 | 11/1991 | European Pat. Off. | 544/258 |
| 2063027 | 7/1971 | Germany . | |
| 1572137 | 7/1980 | United Kingdom | 514/249 |

OTHER PUBLICATIONS

Murakami, Chem. Abstr vol. 77 entry 66198s (1972).
Murakami Chem Abstr vol. 75 entry 64273x (1971).

*Primary Examiner*—Donald G. Daus
*Attorney, Agent, or Firm*—Burns, Doane, Swecker & Mathis

[57] ABSTRACT

There are described ammonium salts of $N^5$-methyl-5,6,7,8-tetrahydrofolic acid as well as processes for their preparation. These ammonium salts may be separated into the single (6R) and (6S)-diastereoisomers. The separated diastereoisomers may be transformed into the corresponding alkali metal or alkaline earth metal salts.

13 Claims, No Drawings

(6R)- AND (6S)-DIASTEREOISOMERS OF AN AMMONIUM SALTS OF $N^5$-METHYL-5,6,7,8-TETRAHYDROFOLIC ACID

This application is a divisional of Application Ser. No. 07/683,772 filed Apr. 11, 1991 now U.S. Pat. No. 5,194,611.

FIELD OF THE INVENTION

The present invention is directed to ammonium salts of N5-methyl-5,6,7,8-tetrahydrofolic acid and to processes for their preparation. This invention is also directed to a process for the separation of the mixture of the (6RS)-diastereoisomers of the ammonium salts of $N^5$-methyl-5,6,7,8-tetrahydrofolic acid into the single (6R) and (6S)-diastereoisomers, as well to their transformation into the corresponding (6R) or (6S)-alkali metal or alkaline earth metal salts.

BACKGROUND OF THE INVENTION $N^5$-Methyl-5,6,7,8-tetrahydrofolic acid, herein sometimes abbreviated with the denotation $N^5$-methyl-THF, is the predominant circulating form of reduced folates in mammals.

There exists an increasing interest for the application of this natural metabolite as at least one active compound in a therapeutical agent, for example as vitamin in folate deficiency states. Therapeutical agents, containing $N^5$-methyl-THF, may also be used for the synergistic exertion of influence of a cancer controlling coumpound and/or for the reduction of the toxicity of a cancer controlling compound and/or for the protection of human and/or animal cells. $N^5$-Methyl-THF in such an agent is usually contained in an amount from 1 mg to 500 mg, especially from 5 mg to 150 mg, per dosis unit. The medicament is preferably in the form of a parenteral and/or oral pharmaceutical preparation. In this regard, reference is made to Cortellaro M., Boschetti C. and Polli E., "High Dose Methotrexate with $N^5$-methyl-THF Rescue in Acute Leukemia and non-Hodgkin's Lymphoma" *Chemioterapia Oncologica* 2 (N.4) (Dec. Suppl./1978) 311; Mazzei T. et al., "High Dose Methotrexate Therapy in High-Risk Trophoblastic Tumors" ibid. 289; Novelli A. et al., Clinical Data on Rescue of "High Dose Methotrexate With $N^5$-methyl-THF in Human Solid Tumors" ibid. 289; Reggev A. and Djerassi I., "Rescue from High-Dose Methotrexate With $N^5$-methyl-THF" *Cancer Treat. Rep.* (1986) 70, 251; and Nigra E. et al., "Can Folates Improve the Efficacy of 5-FU in a Polychemotherapy Schedule?. A New Treatment for Advanced Colorectal Cancer." Fifth NCI-EORT Symposium on New Drugs in Cancer Therapy, Oct. 22–24, 1986, Amsterdam (Oncology Abstracts (1987) 2, 273.

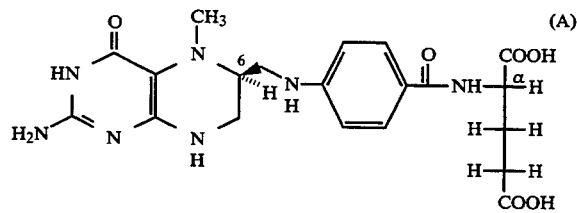

and is defined as (6S, L), where "6S" refers to the configuration at $C_6$ of the pterin-ringsystem and "U" refers to the configuration of the α-carbon atom of the glutamate side chain.

The commercially available forms of $N^5$-methyl-THF, obtained from the chemical reduction of folic acid, are a mixture of the (6RS)-diastereoisomers with the "L"-configuration in the glutamate side chain.

There exists no agreement about the function of the (6R)-diastereoisomer of $N^5$-methyl-THF. It has been assumed, that the unnatural (6R)-diastereoisomer of $N^5$-methyl-THF is inert and is excreted as such in an unchanged form; see, for example D. G. Weir et al., "The Absorption of the Diastereoisomers of $N^5$-methyl-THF in Man: A Carrier-Mediated Process." *Clinical Science and Molecular Medicine* (1973) 45, 625. But there has also been postulated, that the unnatural (6R)diastereoisomer could interfere to the folate transport system through the cell membranes of mammals, including humans; see, for example Chello P.L. et al., "Further Studies of Stereospecificity at Carbon 6 for Membrane Transport of Tetrahydrofolates". *Biochem. Pharmacol.* (1982) 31, 1527; White J.C. et al., "Lack of Stereospecificity at Carbon 6 of $N^5$-methyl-THF Transport in Ehrlich Ascite Tumor Cells." *Journal of Biol. Chem.* (1978) 253, 242–245; and White J.C. and I. D. Goldman, "Lack of Stereospecificity at Carbon 6 of $N^5$-methyl-THF Transport: Possible Relevance to Rescue Regimens with Methotrexate and Leucovorin." *Chemistry and Biology of Pteridines* (Kisliuk/Brown eds./1979), 625.

The individual (6S) and (6R)-diastereoisomers of $N^5$-methyl-THF have been prepared in milligramm amounts of doubtful chemical purity, either by complex enzymatic reactions (see, for example Chello P.L. et al., "Further Studies of Stereospecificity at Carbon 6 for Membrane Transport of Tetrahydrofolates". *Biochem. Pharmacol.* (1982) 31, 1527; or indirect by the reduction of the corresponding $N^5$, $N^{10}$-methylene-THF isomer, which has been obtained by chromatographical separation of the (6RS)-mixture (see White J.C. et al., "Lack of Stereospecificity at Carbon 6 of $N^5$-methyl-THF Transport in Ehrlich Ascite Tumor Cells." *Journal of Biol. Chem.* (1978) 253, 242–245; and Kaufman B.T. et al., "Chromatographic Separation of the Diastereoisomers of dl,L-5,10-methylenetetrahydrofolate." *Journal of Biol. Chem.* (1963) 22, 1498.

5,6,7,8-Tetrahydrofolic acid is herein sometimes abbreviated with the denotation THF.

DESCRIPTION OF THE PRIOR ART

Recently indirect processes for the preparation of the individual diastereoisomers of $N^5$-methyl-THF have been published; see "Verfahren zur Herstellung von Tetrahydrofolaten", European Patent Application No. 0 348 641 (1990), Eprova AG Schaffhausen/CH; and "Derives de l'acide teuffydrofolique, procédé de préparation et utilisation dans la synthese de diastereoisoméres 6S et 6R de folates reduits" French Patent Application No. 90 03032, SAPEC SA Lugano/CH. These processes are based on the fractional cristallisation of $N^5$, $N^{10}$-methenyl-THF.Cl$^-$.HCl of the formula

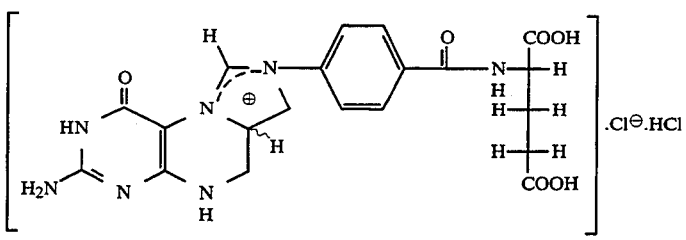

and of $N^5$, $N^{10}$-methenyl-THF $Cl^-$ of the formula

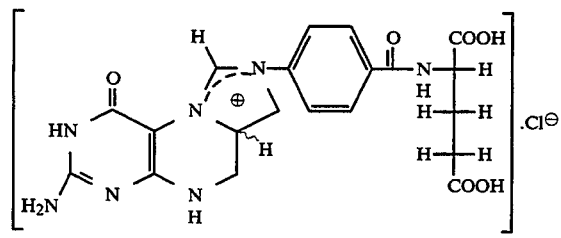

respectively, followed by the chemical transformation of the separated, single (6R) and (6S)-diastereoisomers into $N^5$-methyl-THF. Despite the fact that these processes are practicable in an industrial scale, they have the drawback that they involve several chemical steps, which renders them economically unattractive.

SUMMARY OF THE INVENTION

Hence, it is a general object of the present invention to provide a simple, cheap and efficient process, by which a mixture of (6RS)-diastereoisomers of a $N^5$-methyl-THF-derivative may be separated into the pure, single (6R) and (6S)-diastereoisomers.

Quite surprisingly it was found, that this object may be solved according to this invention by means of a fractional crystallization of novel ammonium salts of a mixture of (6RS)-diastereoisomers of $N^5$-methyl-THF.

In addition to the inventive separation process and, the inventive ammonium salts two inventive processes for the preparation of the ammonium salts are also provided. Still a further inventive process for the preparation of alkali metal or alkaline earth metal salts of (6R) or (6S) $N^5$-methyl-THF from a corresponding inventive diastereoisomer pure ammonium salt is described.

DETAILED DESCRIPTION OF THE PREFERRED EMBODIMENTS

In the first inventive process for the preparation of the inventive ammonium salts, $N^5$-methyl-THF, preferably in the form of the calcium salt, is placed into water. A nitrogen containing base, which then is added, may be a primary or secondary alkyl or aryl amine. Practically, the calcium cation is precipitated by the addition of an oxalic acid as calcium oxalate, which is then filtered off. The aqueous liltrate contains the dissolved ammonium salt. After the evaporation of the water either under reduced pressure or after lyophilization, the ammonium salt is obtained.

In the second inventive process for the preparation of the inventive ammonium salts, $N^5$-methyl-THF, in the form of a carboxylic acid, is preferably placed into water or into a mixture of water and ethanol and/or methanol. In this process the steps of the precipitation of the alkali metal or alkaline earth metal cation and its separation are the same, as has been described in the first inventive process. The other steps of the second inventive process correspond with the corresponding steps of the first inventive process.

The inventive ammonium salts may also be prepared by ion exchange on a corresponding column, on which for, example a calcium cation is exchanged against the desired ammonium ion.

The inventive ammonium salts, for example prepared according to one of the above described processes, are then subjected to a fractional crystallization, wherein the mixture of the (6RS)-diastereoisomers is separated into the single, pure (6R) and (6S)-diastereoisomers. Thereby preferably one part by weight of an inventive ammonium salt is mixed with 5 parts by weight, referred to the above mentioned part per weight of ammonium salt, of a mixture of 85 vol.-% ethanol and 15 vol.-% water. Depending on the nature of the ammonium salt also a heating to a temperature from 40° C. to 60° C. may be necessary in order to obtain a clear solution.

From this clear solution one diastereoisomer is allowed to crystallize, and is then filtered off. The crystallization may be realized at ice water temperature or in a refrigerator or at a temperature from 10° C. to 25° C. If necessary the clear solution may also be treated with seed crystals and then occasionally treated with ultrasonics. The obtained mother liquor is then diluted preferably with ethanol having a low water content. From this diluted solution the other diastereoisomer is allowed to crystallize, and then also filtered off. This second mother liquor may be evaporated and may be subjected to a new fractional crystallization.

Which diastereoisomer crystallizes first depends on the nature of the ammonium salt to be separated. In the case of the $N^5$-methyl-THF-cyclohexyl ammonium salt the (6R)-salt crystallizes first. The (6S)-salt is crystallized from the mother liquor according to the above techniques. In the case of the $N^5$-methyl-THF-diisopropyl ammonium salt the (6S)-salt, crystallizes first. The (6R)-salt is then crystallized from the mother liquor.

The so separated diastereoisomer pure ammonium salts of $N^5$-methyl-THF may be transformed into the alkali metal or alkaline earth metal salts, preferably into the calcium salt or into the magnesium salt. For this a corresponding ammonium salt is dissolved preferably in one part by volume of water. Then an aqueous solution of the desired alkali metal or alkaline earth metal salt is added, for example calcium chloride. In this mixture the pH-value may be adjusted to a value from 6.0 to 7.0. This solution is then cooled to a temperature from 0° C. to 10° C., and is stirred preferably for about one hour. Then 1.5 to 2.5 parts by volume, referred to the above mentioned part by volume of water, of for example ethanol or acetone are added, preferably under stirring during 30 to 90 minutes. Thereby the corresponding alkali metal or alkaline earth metal salt of the $N^5$-methyl-THF precipitates and may be filtered off.

The analysis of an isomeric composition may be carried out in a known way on a chiral HPLC column, See, for example, K. E. Choi and R. L. Schilsky, "Resolution of the Stereoisomers of Leucovorin and $N^5$-methyl-THF by Chiral HPLC." Anal. Biochem. (1988) 168, 398.

Looking now more specifically to the preferred embodiments, one aspect of the invention is ammonium salts of $N^5$-methyl-5,6,7,8-tetrahydrofolic acid of the formula (I)

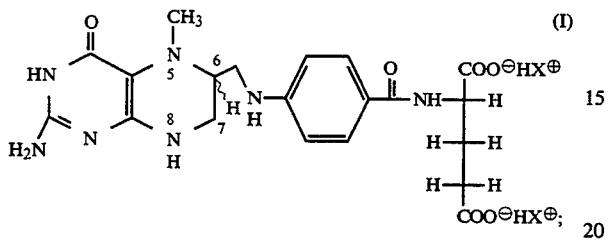

in the form of the mixture of the (6RS)-diastereoisomers, or in the form of the single (6R)-or (6S)-diastereoisomers. In the above formula X is a nitrogen containing base, preferably selected from primary, secondary and tertiary amines and basic amino carboxylic acids, especially selected from the group consisting of cyclohexyl amine, diisopropyl amine, benzyl amine, ammonia, ethanol amine, triethanol amine, 2-dimethyl amino-ethanol, tert.-butyl amine, lysine, especially (L)-lysine, and arginine, especially (L)-arginine.

Another aspect of the invention is a process for the preparation of ammonium salts of (6RS)-$N^5$-methyl-5,6,7,8-tetrahydrofolic acid of formula (I), where X is a nitrogen containing base, preferably selected from primary, secondary and tertiary amines and basic amino carboxylic acids, especially selected from the group consisting of cyclohexyl amine, diisopropyl amine, benzyl amine, ammonia, ethanol amine, triethanol amine, 2-dimethyl amino-ethanol, tert.-butyl amine, lysine, especially (L)-lysine, and arginine, especially (L)-arginine. According to the process, (6RS)-$N^5$-methyl-5,6,7,8-tetrahydrofolic acid, in the form of an alkali metal or alkaline earth metal salt, especially a $Ca^{2+}$ or $Mg^{2+}$ salt, is placed into a solvent, preferably water. Then, a nitrogen containing base is added, preferably in an amount from 2 to 2.5 molequivalents. The base is preferably selected of from primary, secondary and tertiary amines and basic amino carboxylic acids, especially those selected from the group, consisting of cyclohexyl amine, diisopropyl amine, benzyl amine, ammonia, ethanol amine, triethanol amine, 2-dimethyl amino-ethanol, tert.-butyl amine, lysine, especially (L)-lysine, and arginine, especially (L)-arginine. Then the process involves transforming to a substantially insoluble salt or precipitate of the above mentioned salt of the alkali metal or alkaline earth metal cation by the addition of a suitable acid such as sulfuric acid or oxalic acid. The substantially insoluble salt is then separated by means of filtration, followed by removing the solvent, for example, by means of evaporation under reduced pressure or by means of lyophilization.

Another embodiment of the invention is another process for the preparation of ammonium salts of (6RS)-$N^5$-methyl-5,6,7,8-tetrahydrofolic acid of formula (I) where X is a nitrogen containing base, preferably selected from primary, secondary and tertiary amines and basic amino carboxylic acids, especially selected from the group consisting of cyclohexyl amine, diisopropyl amine, benzyl amine, ammonia, ethanol amine, triethanol amine, 2-dimethyl amino-ethanol, tert.-butyl amine, lysine, especially (L)-lysine, and arginine, especially (L)-arginine. According to the process, (6RS)-$N^5$-methyl-5,6,7,-tetrahydrofolic acid is placed into at least one solvent, preferably water. Then, a nitrogen containing base, preferably in an amount from 2 to 2.5 molequivalents, is added. The base is preferably selected from primary, secondary and tertiary amines as well as basic amino carboxylic acids, especially selected from the group consisting of cyclohexyl amine, diisopropyl amine, benzyl amine, ammonia, ethanol amine, triethanol amine, 2-dimethyl amino-ethanol, tert.-butyl amine, lysine, especially (L)lysine, and arginine, especially (L)-arginine. Then, the solvent(s) is (are) removed by, for example, means of evaporation under reduced pressure or by means of lyophilization.

Even another embodiment relates to a process for the separation of the mixture of (6RS)-diastereoisomers of an ammonium salt of $N^5$-methyl-5,6,7,8-tetrahydrofolic acid of formula (I) into the single (6R) and (6S)-diastereoisomers where X is a nitrogen containing base, preferably selected from primary, secondary and tertiary amines as well as basic amino carboxylic acids, especially selected from the group, consisting of cyclohexyl amine, diisopropyl amine, benzyl amine, ammonia, ethanol amine, triethanol amine, 2-dimethyl amino-ethanol, tert.-butyl amine, lysine, especially (L)-lysine, and arginine, especially (L)-arginine. According to the process, a mixture of (6RS)diastereoisomers, especially in solid form, is mixed with a mixture A of solvents, containing water and at least one water miscible solvent, preferably a polar solvent, especially monovalent or polyhydric alcohols with 1 to 5 carbon atoms (e.g., ethanol), and then transforming the prepared mixture into a clear solution, for example, by means of heating to a temperature from 40° C. to 60° C. Then, one diastereoisomer is allowed to crystallize and is separated.

Thereafter, the mother liquor is diluted with the above mentioned water miscible solvent(s) and the other diastereoisomer is allowed to crystallize and is separated from the diluted solution.

The aforementioned mixture A of solvents preferably contains from 50 to 95 vol. -%, preferably from 75 to 95 vol. -%, especially 85 vol.-% of ethanol, and, as residue water. It is most preferred that from 3 to 10 parts by volume, especially about 5 parts by volume, of mixture A of solvents are used per 1 part by weight of the mixture of (6RS)-diastereoisomers.

According to the aforementioned process, it is also preferred that the clear solution be treated with seed crystals, and optionally, but also preferred that the solution treated with seed crystals be treated with ultrasonics.

Another embodiment of the invention relates to a process for the preparation of alkali metal or alkaline earth metal salts of (6R) or (6S)-$N^5$-methyl-5,6,7,8-tetrahydrofolic acid of the formulae (IIa) or (IIb):

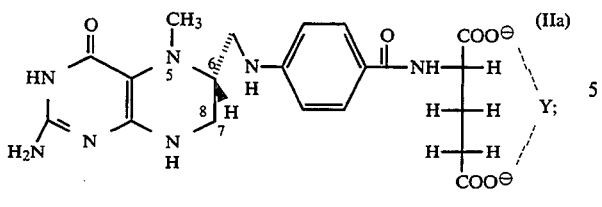

(IIa)

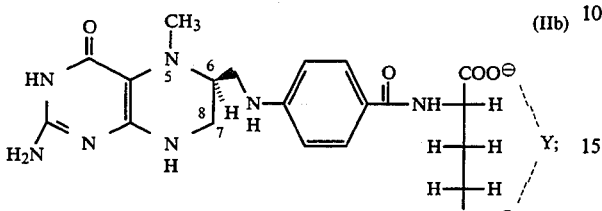

(IIb)

wherein Y is defined as two alkali metal cations, or as one alkaline earth metal cation, especially $Ca^{2+}$ or $Mg^{2+}$. According to the process, the corresponding diastereoisomer pure ammonium salt of $N^5$-methyl-5,6,7,8-tetrahydrofolic acid of the formulae (Ia) or (Ib)

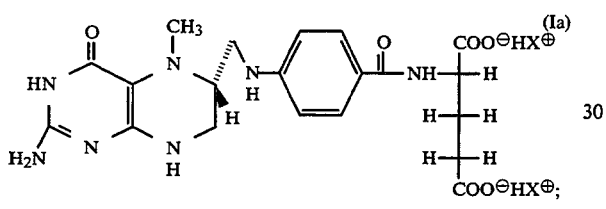

(Ia)

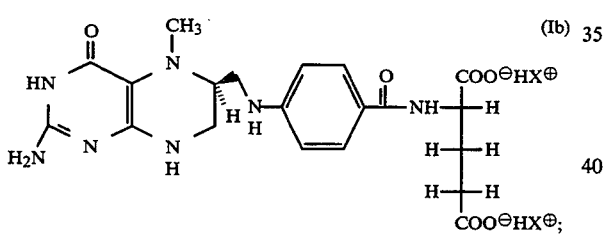

(Ib)

where X is a nitrogen containing base, preferably selected from primary, secondary and tertiary amines and basic amino carboxylic acids, especially selected from the group consisting of cyclohexyl amine, diisopropyl amine, benzyl amine, ammonia, ethanol amine, triethanol amine, 2-dimethyl amino-ethanol, tert.-butyl amine, lysine, especially (L)-lysine, and arginine, especially (L)-arginine, is optionally, but preferably prepared according to the aforementioned process.

The salt is then dissolved in one part by volume of water, and then, an aqueous solution of an alkali metal or alkaline earth metal salt is added, preferably a corresponding halide, especially the corresponding chlorides, for example $caCl_2$ or $MgCl_2$. The resulting mixture, Mixture B, is stirred, preferably at a temperature in the range from 0° C. to 10° C., for example, for about one hour. Then, the process involves adding 1.5 to 2.5 parts by volume of at least one polar, water miscible organic solvent, preferably ethanol or acetone, preferably under stirring during 30 to 90 minutes, and separating the precipitated alkali metal or alkaline earth metal salt of the formulae (IIa) or (IIb).

In the above process, it is preferred that the pH of Mixture B is adjusted to a value in the range from 6.0 to 7.0.

In another aspect of the invention there is provided a medicament for the treatment and/or the control of human and/or animal tumors and/or for the synergistic exertion of influence of a cancer controlling compound and/or for the reduction of the toxicity of a cancer controlling compound and/or for the protection of human and/or animal cells. The medicament is characterized in that it contains as at least one active compound of at least one ammonium salt of $N^5$-methyl-5,6,7,8-tetrahydrofolic acid of the formula (I'):

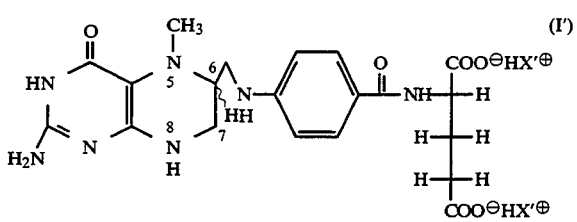

(I')

in the form of the mixture of the (6RS)-diastereoisomers or in the form of the single (6R)-or (6S)-diastereoisomers, wherein X' is a pharmacological acceptable, nitrogen containing base, preferably selected from primary, secondary and tertiary amines, and basic amino carboxylic acids, especially selected from the group consisting of ethanolamine, triethanolamine, 2-dimethylamino-ethanol, tert.-butylamine, lysine, especially (L)-lysine, and arginine, especially (L)-arginine; and/or at least one alkali metal and/or alkaline earth metal salt of (6R) or (6S) $N^5$-methyl-5,6,7,8-tetrahydrofolic acid of the formulae (IIa) or (IIb)

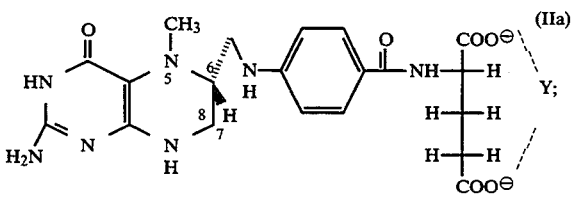

(IIa)

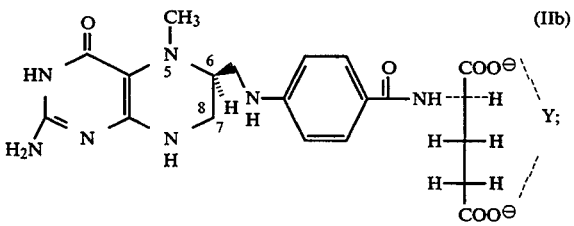

(IIb)

wherein Y is defined as two alkali metal cations or as one alkaline earth metal cation, especially $Ca^{2+}$ or $Mg^{2+}$. They are preferably present in an amount from 1 mg to 500 mg, especially from 5 mg to 150 mg, per dosis unit, and the medicament is preferably in the form of a parenteral and/or oral pharmaceutical preparation.

Another aspect of the invention relates to the use of the ammonium salts of $N^5$-methyl-5,6,7,8-tetrahydrofolic acid of formula (I'), and/or of the alkali metal and/or alkaline earth metal salts of (6R) or (6S) $N^5$-methyl-5,6,7,8-tetrahydrofolic acid of formulae (IIa) or (IIb) in a single form or in any combination for the preparation of a medicament for the treatment and/or the control of human and/or animal tumors and/or for the synergistic exertion of influence of a cancer controlling compound and/or for the reduction of the toxicity of a cancer controlling compound and/or the protection of human and/or animal cells. The salts are preferably present in the medicament in an amount from 1 mg to 500 mg, especially from 5 mg to 150 mg, per dosis unit, and the medicament is preferably in the form of a parenteral and/or oral, pharmaceutical preparation.

The following examples illustrate the present invention.

Example 1

Preparation of (6RS)-$N^5$-methyl-THF-cyclohexyl ammonium salt

To a suspension of 100 g of (6RS)-$N^5$-methyl-THF-calcium salt in 800 ml of water, which was stirred at a temperature of 40° C. under a nitrogen atmosphere, were added 40 g of cyclohexylamine. The temperature was rised to 60° C., and a clear solution was obtained. Then 24 g of oxalic acid dihydrate in 200 ml of water were added, and this mixture was stirred at a temperature of 0° C. during 30 minutes. After the removal of the formed calcium oxalate by means of centrifugation the supernatant solution was evaporated at a temperature of 50° C. under reduced pressure. There was obtained crude (6RS)-$N^5$-methyl-THF-cyclohexyl ammonium salt in the form of a honey-like or glass-like solid. The HPLC analysis of this product showed one single peak.

Example 2

Separation of the mixture of (6RS)-diastereoisomers of $N^5$-methyl-THF-cyclohexyl ammonium salt A: (6R)-$N^5$-Methyl-THF-cyclohexyl ammonium salt The crude (6RS)-$N^5$-methyl-THF-cyclohexyl ammonium salt, prepared according to example 1, was dissolved in 550 ml of a mixture of 85 parts by volume of ethanol and 15 parts by volume of water at a temperature of 60° C. The formed clear solution was cooled to room temperature and treated with seed crystals of crystalline (6R)-$N^5$-methyl-THF-cyclohexyl ammonium salt, obtained from a previous batch. After stirring at room temperature over night and at a temperature of 10° C. during 4 hours the obtained crystalline solid was isolated by means of filtration. This solid was washed once with 85 ethanol and dried under reduced pressure at a temperature of 50° C. during 2 hours. There were obtained 30.9 g of (6R)-$N^5$-methyl-THF-cyclohexyl ammonium salt.

$[\alpha]_D = -7.3°$ (c=1 in 0,01 N NaOH)

The analysis on a RESOLVOSIL-column showed a ration of diastereoisomers of (6R)/(6S)=96.5/3.5 (see K. E. Choi and R. L. Schilsky, "Resolution of The Stereoisomers of Leucovorin and $N^5$-methyl-THF by Chiral HPLC." Anal. Biochem., (1988) 168, 398.

The HPLC analysis on a "reverse phase"-column showed that this product was 100% pure.

IR (KBr/cm$^{-1}$): 3300, 2950, 2860, 1660, 1610, 1390.

| elemental analysis | calculated (%) (Dihydrate) | found (%) |
|---|---|---|
| C | 55.42 | 55.72 |
| H | 7.99 | 7.86 |
| N | 18.46 | 18.32 |

B: (6S)-$N^5$-Methyl-THF-cyclohexyl ammonium salt

The mother liquor of the filtration described in item A was diluted with 1200 ml absolute ethanol. The obtained solution was treated with authentic seed crystals of (6S)-$N^5$-methyl-THF-cyclohexyl ammonium salt. The mixture was allowed to stand during 24 hours at room temperature. The obtained crystalline solid was isolated by means of filtration. This solid was washed once with 94% ethanol and dried under reduced pressure at a temperature of 50° C. There were obtained 23.7 g of (6S)-$N^5$-methyl-THF-cyclohexyl ammonium salt.

$[\alpha]_D = +30.6°$ (c=1 in 0.01 N NaOH)

The analysis on a RESOLVOSIL-column showed a ration of diastereoisomers of (6R)/(6S)=3/97 (see K. E. Choi and R. L. Schilsky, "Resolution of The Stereoisomers of Leucovorin and $N^5$-methyl-THF by Chiral HPLC. Anal. Biochem. (1988) 168, 398.

The HPLC analysis on a "reverse phase"-column showed that this product was 100% pure.

IR (KBr/cm$^{-1}$): 3300, 2940, 2860, 1610, 1390.

| elemental analysis | calculated (%) (Dihydrate) | found (%) |
|---|---|---|
| C | 55.42 | 55.72 |
| H | 7.99 | 7.86 |
| N | 18.46 | 18.32 |

Example 3

Preparation of (6S)-$N^5$-methyl-THF-calcium salt 15.0 g of (6S)-$N^5$-Methyl-cyclohexyl ammonium salt were dissolved in 120 ml of water and stirred at room temperature under a nitrogen atmosphere. After the addition of 9.9 ml of 2M calcium chloride solution the pH-value was adjusted to a value of 6.8 by the addition of 1 N NaOH. The obtained mixture was stirred at a temperature of 0° C. during 1 hour. Then were added 240 ml of ethanol during 40 minutes. The obtained crystalline solid was isolated by means of filtration. This solid was washed with 85% ethanol and dried under reduced pressure at a temperature of 50° C. There were obtained 10.4 g of (6S)-$N^5$-methyl-THF-calcium salt.

The HPLC analysis on a "reverse phase"-column showed that this product was 100% pure.

$[\alpha]_D = +40°$ (c=1/1% NH$_4$OAc, pH 6.0) UV (20 mg/l in 1% NH$_4$OAc, pH 6.0):

$\lambda_{max} = 290$ nm ($\epsilon = 28600$)

$\lambda_{min} = 245$ nm $A_{max}/A_{min} = 3.7$

The analysis on a RESOLVOSIL-column showed a ratio of diastereoisomers of (6R)/(6S)=3/97 (see K. E. Choi and R. L. Schilsky, "Resolution of The Stereoisomers of Leucovorin and $N^5$-methyl-THF by Chiral HPLC. Anal. Biochem. (1988) 168, 398.

Example 4

Preparation of (6R)-$N^5$-methyl-THF-calcium salt

Starting from (6R)-$N^5$-methyl-THF-cyclohexyl ammonium salt the title product was prepared in an analogous way as described in example 3.

The HPLC analysis on a "reverse phase"-column showed that the product was 100% pure.

$[\alpha]_D = -4.7°$ (c=1/1% NH$_4$OAc, pH 6.0) UV (20 mg/l in 1% NH$_4$OAc, pH 6.0):

$\lambda_{max} = 290$ nm ($\epsilon = 30200$)

$\lambda_{min} = 245$ nm $A_{max}/A_{min} = 3.6$

The analysis on a RESOLVOSIL-column showed a ratio of diastereoisomers of (6R)/(6S)=97/3 (see K. E. Choi and R. L. Schilsky, "Resolution of The Stereoisomers of Leucovorin and $N^5$-methyl-THF by Chiral HPLC." *Anal. Biochem.* (1988) 168, 398.

Example 5

Preparation of (6RS)-$N^5$-methyl-THF-diisopropyl ammonium salt

To a suspension of 5.0 g of (6RS)-$N^5$-methyl-THF-calcium salt in 40 ml of water, which was stirred at a temperature of 40° C. under a nitrogen atmosphere, were added 2.03 g of diisopropylamine. The temperature was increased to about 55° C., and a clear solution was obtained. After the cooling to room temperature a solution of 1.2 g of oxalic acid dihydrate in 10 ml of water was added, and this mixture was stirred at a temperature of 0° C. during 30 minutes. After the removal of the formed calcium oxalate by means of centrifugation the supernatant solution was evaporated at a temperature of 70° C. under reduced pressure. There was obtained crude (6RS)-$N^5$-methyl-THF-diisopropyl ammonium salt in the form of a honey-like or glass-like solid. The HPLC analysis of this product showed a single peak.

Example 6

Separation of the mixture of (6RS)-diastereoisomers of $N^5$-methyl-THF-diisopropyl ammonium salt; isolation of (6S)-$N^5$-methyl-THF-diisopropyl ammonium salt The crude (6RS)-$N^5$-methyl-THF-diisopropyl ammonium salt, prepared according to example 5, was dissolved in 27 ml of a mixture of 85 parts by volume of ethanol and 15 parts by volume of water at a temperature of 60° C. The formed clear solution was cooled to room temperature and stirred at this temperature during 48 hours. The obtained solid was isolated by means of centrifugation. This solid was washed once with 85% ethanol and dried under reduced pressure at a temperature of 50° C. during 2 hours. There were obtained 1.07 g of (6S)-$N^5$-methyl-THF-diisopropyl ammonium salt.

The analysis on a RESOLVOSIL-column showed a ratio of diastereoisomers of (6R)/(6S)=90/10 (see K. E. Choi and R. L. Schilsky, "Resolution of The Ptereoisomers of Leucovorin and $N^5$-methyl-THF by Chiral HPLC." Anal. Biochem. (1988) 168, 398.

Example 7

Preparation of (6RS)-$N^5$-methyl-THF.2-hydroxyethyl ammonium salt

To a stirred suspension of 15 g of (6RS)-$N^5$-methyl-THF in 100 ml of 85% ethanol were added drop by drop 3.9 ml of ethanolamine, whereby an oily suspension was obtained.

This suspension was stirred vigorously during 3 hours at a temperature of 0° C., and the formed crystalline solid was occasionally reduced to small pieces with a spatula.

Then the product was isolated by filtration, washed with absolute ethanol and dried under reduced pressure at a temperature of 50° C. during 90 minutes. There were obtained 16.0 g of (6RS)-$N^5$-methyl-THF.2-hydroxy-ethyl ammonium salt.

The HPLC analysis on a "reverse phase"-column showed that this product was 96.5% pure.

UV (20 mg/l in 1% NH$_4$OAc, pH 6.0):

$\lambda_{max} = 290$ nm $\lambda_{min} = 245$ nm $A_{max}/A_{min} = 3.55$

IR (KBr/cm$^{-1}$): 3360, 2940, 2860, 1610, 1390, 1330.

Example 8

Acute intravenous toxicity studies in mice

| Compound | LD$_{50}$(mg/kg) |
|---|---|
| (6RS)-$N^5$-Methyl-THF.Ca$^{2+}$ | 339 |
| (6S)-$N^5$-Methyl-THF.Ca$^{2+}$ | 847 |
| (6R)-$N^5$-Methyl-THF.Ca$^{2+}$ | 460 |

Example 9

Inhibition of the growth of human CCRF-CEM cells

Human leukemia cells (CCRF-CEM) were grown during 72 hours in the presence of increasing concentration of (6R)-$N^5$-methyl-THP.Ca$^{2+}$. The following Table shows the percentual cellular growth related to the control experiment.

| Concentration of (6R)-$N^5$-methyl-THF.Ca$^{2+}$ [μM] | % growth (72 hrs exp.) |
|---|---|
| 0 (control) | 100 |
| 1 | 95 |
| 10 | 99 |
| 30 | 10 |
| 100 | 9.3 |

-continued

| Concentration of (6R)-N⁵-methyl-THF.Ca²⁺ [μM] | % growth (72 hrs exp.) |
|---|---|
| 250 | 8.2 |

While there are shown and described present preferred embodiments of the invention, it is to be distinctly understood that the invention is not limited thereto, but may be otherwise variously embodied and practiced within the scope of the following claims.

We claim:

1. An ammonium salt of $N^5$-methyl-5,6,7,8-tetrahydrofolic acid of formula I:

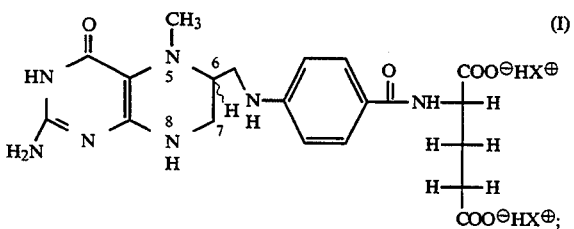

in the form of the single (6R)- or (6S)-diastereoisomers, wherein

X is cyclohexyl amine, diisopropyl amine, benzyl amine, ammonia, ethanol amine, triethanol amine, 2-dimethyl amino-ethanol, tert-butyl amine, lysine, or arginine.

2. An ammonium salt according to claim 1, wherein said lysine is (L)-lysine, and said arginine is (L)-arginine.

3. An ammonium salt of $N^5$-methyl-5,6,7,8-tetrahydrofolic acid of formula I according to claim 1, in the form of the single (6R)-diastereoisomer.

4. An ammonium salt of $N^5$-methyl-5,6,7,8-tetrahydrofolic acid of formula I according to claim 1, in the form of the single (6S)-diastereoisomer.

5. A medicament for the treatment of at least one of the control of human and/or animal tumors, for the synergistic exertion of influence of a cancer controlling compound, for the reduction of the toxicity of a cancer controlling compound, and for the protection of human and/or animal cells, said medicament consisting essentially of, in an effective amount to control of human and/or animal tumors, for the synergistic exertion of influence of a cancer controlling compound, for the reduction of the toxicity of a cancer controlling compound, or for the protection of human and/or animal cells, the single (6R)- or (6S)-diastereoisomers of an ammonium salt of $N^5$-methyl-5,6,7,8-tetrahydrofolic acid of formula I:

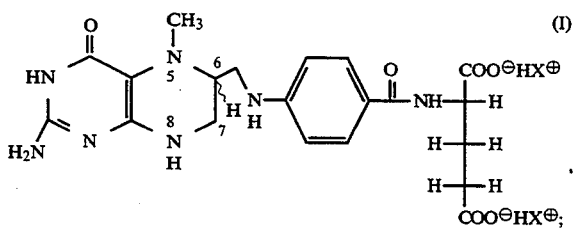

wherein

X is cyclohexyl amine, diisopropyl amine, benzyl amine, ammonia, ethanol amine, triethanol amine, 2-dimethyl aminoethanol, tert-butyl amine, lysine, or arginine.

6. A medicament according to claim 5 in the form of a parenteral or oral pharmaceutical preparation.

7. A medicament according to claim 5, said medicament comprising from 5 to 150 mg per dose unit of said an ammonium salt of $N^5$-methyl-5,6,7,8-tetrahydrofolic acid of formula I.

8. A medicament according to claim 5, with an ammonium salt of $N^5$-methyl-5,6,7,8-tetrahydrofolic acid of formula I in the form of the single (6R) diastereoisomer.

9. A medicament according to claim 5, with an ammonium salt of $N^5$-methyl-5,6,7,8-tetrahydrofolic acid of formula I in the form of the single (6S) diastereoisomer.

10. An ammonium salt of $N^5$-methyl-5,6,7,8-tetrahydrofolic acid of formula I:

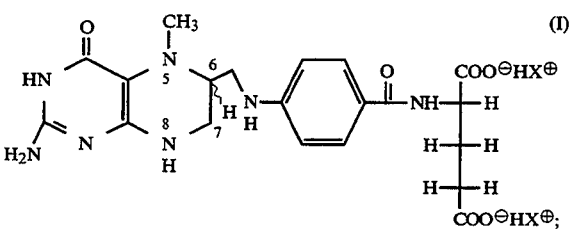

wherein said salt is a (6RS)-N(5)-methyl-5,6,7,8-tetrahydrofolic acid-bis-cyclohexyl ammonium salt.

11. A medicament for the treatment of at least one of the control of human and/or animal tumors, for the synergistic exertion of influence of a cancer controlling compound, for the reduction of the toxicity of a cancer controlling compound, and for the protection of human and/or animal cells, said medicament consisting essentially of, in an effective amount to control of human and/or animal tumors, for the synergistic exertion of influence of a cancer controlling compound, or for the protection of human and/or animal cells, an ammonium salt of $N^5$-methyl-5,6,7,8-tetrahydrofolic acid of formula I:

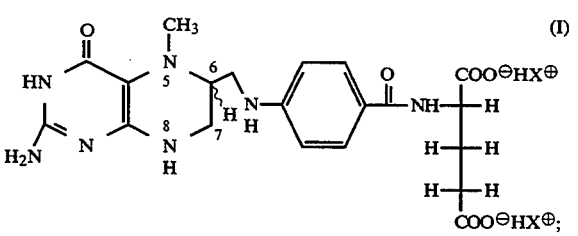

wherein said ammonium salt of $N^5$-methyl-5,6,7,8-tetrahydrofolic acid of formula I is a (6RS)-N(5)-methyl-5,6,7,8-tetrahydrofolic acid-bis-cyclohexyl ammonium salt.

12. A medicament according to claim 11 in the form of a parenteral or oral pharmaceutical preparation.

13. A medicament according to claim 11, said medicament comprising from 5 to 150 mg per dose unit of said an ammonium salt of $N^5$-methyl-5,6,7,8-tetrahydrofolic acid of formula I.

* * * * *